US007943377B2

(12) United States Patent
Carnes et al.

(10) Patent No.: US 7,943,377 B2
(45) Date of Patent: May 17, 2011

(54) PROCESS FOR PLASMID DNA FERMENTATION

(75) Inventors: Aaron E. Carnes, Lincoln, NE (US); James A. Williams, Lincoln, NE (US)

(73) Assignee: Nature Technology Corp., Lincoln, NE (US)

(*) Notice: Subject to any disclaimer, the term of this patent is extended or adjusted under 35 U.S.C. 154(b) by 788 days.

(21) Appl. No.: 11/573,825

(22) PCT Filed: Aug. 16, 2005

(86) PCT No.: PCT/US2005/029238
§ 371 (c)(1),
(2), (4) Date: Feb. 16, 2007

(87) PCT Pub. No.: WO2006/023546
PCT Pub. Date: Mar. 2, 2006

(65) Prior Publication Data
US 2007/0254342 A1 Nov. 1, 2007

Related U.S. Application Data

(60) Provisional application No. 60/603,000, filed on Aug. 19, 2004.

(51) Int. Cl.
*C12N 5/02* (2006.01)
(52) U.S. Cl. .................... 435/375; 435/383; 435/320.1
(58) Field of Classification Search .................. None
See application file for complete search history.

(56) References Cited

U.S. PATENT DOCUMENTS

| 5,955,323 | A | 9/1999 | Chen |
| 6,503,738 | B1 | 1/2003 | Thatcher et al. |
| 6,664,078 | B1 | 12/2003 | Schmidt et al. |
| 2004/0142452 | A1 | 7/2004 | Soubrier |
| 2005/0026177 | A1 | 2/2005 | Urthaler et al. |

FOREIGN PATENT DOCUMENTS

| WO | 0028048 A1 | 5/2000 |

OTHER PUBLICATIONS

Lahijani R, High Yield Production of pBR322-Derived Plasmids Inteded for Human Gene Therapy by Employing a Temperature-Controllable Point Mutation, Oct. 20, 1996, Human Gene Therapy, vol. 7, pp. 1971-1980.
FDA Points to Consider on Plasmid DNA Vaccines for Preventive Disease Indications, 1996.
Birnboim, A Rapid Alkaline Extraction Procedure for Screening Recombinant Plasmid DNA, 1979, Nucleic Acids Res. 7, pp. 1513-1523.
Goldstein et al, Regulation of Bacterial DNA Supercoiling: Plasmid Linking Number Vary with Growth Temperature, Jul. 1984, Proc Nat. Acad Sci USA, Biochemistry, vol. 81, pp. 4046-4050.
Dorman et al, DNA Supercoiling and the Anaerobic and Growth Phase Regulation of tonB Gene Expression, Jun. 1988, Journal of Bacteriology, vol. 170, No. 6, pp. 2816-2826.
Hopkins et al, Effects of Dissolved Oxygen Shock on the Stability of Recombinant *Escherichia coli* Containing Plasmid pKN401, 1987, Biotechnology and Bioengineering, vol. 29, pp. 85-91.
Namdev et al, Effect of Oxygen Fluctuations on Recombinant *Escherichia coli* Fermentation, 1993, Biotechnology and Bioengineering, vol. 41, pp. 666-670.
Durland et al, Manufacturing and Quality Control of Plasmid-Based Gene Expression Systems, 1998, Advanced Drug Delivery Reviews, vol. 30, pp. 33-48.
Wong et al, Temperature-Sensitive Copy Number Mutants of ColE1 Are Located in an Untranslated Region of the Plasmid Genome, Jun. 1982, Proc Natl Acad Sci USA, Genetics, vol. 79, pp. 3570-3574.
Lin-Chao et al, High Copy Number of the pUC Plasmid Results From a Rom/Rop-Suppressible Point Mutation in RNA II, 1992, Molecular Microbiology, vol. 6, No. 22, pp. 3385-3393.
Seo et al, Effects of Recombinant Plasmid Content on Growth Properties and Cloned Gene Product Formation in *Escherichia coli*, 1985, Biotechnology and Bioengineering, vol. 27, pp. 1668-1674.
Robinow et al, The Bacterial Nucleoid Revisited, Jun. 1994, Microbiological Reviews, vol. 58, No. 2, pp. 211-232.
Setlow et al, Synthesis of a *Bacillus subtilis* Small, Acid-Soluble Spore Protein in *Escherichia coli* Causes Cell DNA to Assume Some Characteristics of Spore DNA, Mar. 1991, Journal of Bacteriology, vol. 173, No. 5, pp. 1642-1653.
Frenkeil-Krispin et al, Regulated Phase Transitions of Bacterial Chromatin: A Non-Enzymatic Pathway for Generic DNA Protection, 2001, The EMBO Journal, vol. 20, No. 5, pp. 1184-1191.
Carnes, Fermentation Design for the Manufacture of Therapeutic Plasmid DNA, Oct. 2005, Bioprocess International, vol. 3, No. 9.
Arends et al, Inhibiting Cell Division in *Escherichia coli* Has Little if Any Effect on Gene Expression, Feb. 2004, Journal of Bacteriology, vol. 186, No. 3, pp. 880-884.
Satyangal et al, A Generalized Model of Plasmid Replication, 1989, Biotechnology and Bioengineering, vol. 33, pp. 1135-1144.
FDA Points to Consider in the characterization of cell lines used to produce biologics, 1993.

*Primary Examiner* — James S Ketter
(74) *Attorney, Agent, or Firm* — Brooks Kushman P.C.

(57) ABSTRACT

Improvements in plasmid DNA production technology are needed to insure the economic feasibility of future DNA vaccines and DNA therapeutics. General methods are described, by means of which it is possible to dramatically increase plasmid DNA productivity in a fermentor. These processes feature Fed-batch fermentation strategies, combined with novel growth and induction phase temperature shifts.

7 Claims, 5 Drawing Sheets

PROCESS FOR PLASMID DNA FERMENTATION

CROSS-REFERENCE TO RELATED APPLICATION

This application claims the benefit of U.S. provisional application Ser. No. 60/603,000 filed 19 Aug. 2004.

STATEMENT REGARDING FEDERALLY SPONSORED RESEARCH OR DEVELOPMENT

Not Applicable

FIELD OF THE INVENTION

The present invention relates to the production of covalently closed circular (ccc) recombinant DNA molecules such as plasmids, cosmids, bacterial artificial chromosomes (BACs), bacteriophages, viral vectors and hybrids thereof, and more particularly is a method for production of the said DNA molecules at high levels in fermentation culture.

BACKGROUND OF THE INVENTION

The present invention relates to the production of covalently closed circular (ccc) recombinant DNA molecules. Such molecules are useful in biotechnology, transgenic organisms, gene therapy, therapeutic vaccination, agriculture and DNA vaccines.

With the invention in mind, a search of the prior art was conducted. E. coli plasmids have long been the single most important source of recombinant DNA molecules used by researchers and by industry. Today, plasmid DNA is becoming increasingly important as the next generation of biotechnology products (gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines. Plasmids are also utilized in gene therapy or gene replacement applications, wherein the desired gene product is expressed from the plasmid after administration to the patient.

Today, the FDA standards are not defined except in preliminary form (see: FDA Points to Consider on Plasmid DNA Vaccines for Preventive Infectious Disease Indications, 1996). However, in the future, international standards for plasmid DNA purity are likely to be the same or very similar to those that are used for recombinant protein products similarly produced from E. coli fermentation, and such standards exceed the current purity attainable from established methods. Most glaringly, the accepted standard of <100 pg host genomic DNA per dose (see: FDA Points to consider in the characterization of cell lines used to produce biologics, 1993) is far below the levels currently attainable for purified plasmid preparations (100 pg per 1 mg dose is equivalent to one part per ten million).

The basic methods for obtaining plasmids (by bacterial fermentation), and for their purification (e.g., by the alkaline lysis method (Bimboim, H C, Doly J. 1979, *Nucleic Acids Res.* 7: 1513-1523)) are well-known. Initially, the fermented bacterial cell paste is resuspended and lysed (using a combination of sodium hydroxide and sodium dodecylsulfate), after which the solution is neutralized by the addition of acidic salt (e.g., potassium acetate), which precipitates the bacterial DNA and the majority of cell debris. The bulk of super-coiled plasmid DNA remains in solution, along with contaminating bacterial RNA, DNA and proteins, as well as E. coli endotoxin (lipopolysaccharide, or LPS). The soluble fraction is then separated by filtration and subjected to a variety of purification steps, which may include: RNase digestion; chromatography (ion exchange gel filtration, hydroxyapatite, gel filtration, hydrophobic interaction, reverse phase, HPLC, etc.); diafiltration; organic extraction, selective precipitation, etc.

Clearly, increasing the purity of the starting material and achieving better downstream purification are essential goals for manufacturing clinical grade DNA on an industrial scale.

Fermentation Media Considerations

Design of a balanced medium is based on the cell's energy requirements and elemental composition.

Typically, the nutritional requirements are satisfied by either minimal media or semi-defined media.

Semi-defined media contain complex components such as yeast extract, casamino acids, and peptones. The addition of complex components supplies growth factors, amino acids, purines and pyrimidines and often supports higher cell densities.

Carbon accounts for half of the cellular composition. Accordingly, carbon is included in the highest amounts. The carbon source provides energy and biomass, and is usually utilized as the limiting nutrient. Glucose is the conventional carbon source. It is metabolized very efficiently and therefore gives a higher cellular yield. However, high glucose concentrations cause undesirable acetate production due to metabolic overflow (known as the Crabtree effect). Glycerol is also used and is often the preferred carbon source in batch cultures. Although cellular yields from glycerol are slightly smaller than from glucose, glycerol does not cause as high of levels of acetate production and can be used at higher concentrations without being inhibitory. Glycerol also supports reduced maximum specific growth rates.

The requirement for nitrogen may be satisfied by inorganic or organic nitrogen sources. Ammonia and ammonium salts (e.g. $NH_4Cl$, $(NH_4)_2SO_4$) are used in minimal media. Semi-defined media supply nitrogen either partly or entirely from complex components, including yeast extract, peptones, and casamino acids.

Minerals are required for growth, metabolism, and enzymatic reactions. Magnesium, phosphorus, potassium, and sulfur are typically added as distinct media components. Di- and monopotassium phosphates provide potassium and phosphorous and also function as buffering agents in certain proportions. Magnesium sulfate heptahydrate is often used as the source of magnesium and sulfur. Other essential minerals include calcium, copper, cobalt, iron, manganese, molybdenum and zinc. These are required in smaller amounts and are often supplied by addition of a trace minerals solution, though they are usually present as impurities in the major ingredients. Osmolarity is adjusted with sodium chloride.

The use of animal-derived products, and in particular bovine products, in plasmid manufacture is unacceptable due to the risk of prion or virus contamination. All media components should be certified animal product free. Vegetable-derived substitutes are available for many components which have animal origin (e.g. vegetable glycerol, soy peptone).

Plasmid Fermentation Process Considerations

Growth Rate

The use of reduced growth rate is the unifying principle in high quality, high yield plasmid fermentations. High growth rates have been associated with acetate production, plasmid instability, and lower percentages of super-coiled plasmid. A reduced growth rate alleviates growth rate-dependent plasmid instability by providing time for plasmid replication to synchronize with cell division.

Growth Conditions

Fermentation gives us the ability to control and monitor many of the parameters that affect plasmid quality and yield. Super-coiling is known to be affected by oxygen and temperature (Dorman C J et al. 1988 *J. Bacteriol.* 179: 2816-2826), (Goldstein E, Drlica K. 1984 *Proc Natl Acad Sci USA.* 81: 4046-4050). Oxygen has been shown to play a role in plasmid stability. One study (Hopkins D J, Betenbaugh M J, Dhurjati P. 1987 *Biotechnol Bioeng.* 29: 85-91) found that a single drop in dissolved oxygen concentration to 5% of air saturation led to rapid loss in plasmid stability. Another study (Namdev P K, Irwin N, Thompson B G, Gray M R. 1993 *Biotechnol Bioeng.* 41: 666-670) showed that fluctuations in oxygen input lead to plasmid instability. Furthermore, the formation of nicked plasmids and multimers can be affected by many parameters, including temperature, pH, dissolved oxygen, nutrient concentration, and growth rate (Durland R H, Eastman E M. 1998 *Adv Drug Deliver Rev.* 30: 33-48). The optimal temperature for *E. coli* growth is 37° C. However, lower temperatures (30-37° C.) may be used in batch fermentation to cause a reduced maximum specific growth rate. Higher temperatures (36-45° C.) can also be employed to induce selective plasmid amplification with some replication origins such as pUC, and pMM1 (Wong E M, Muesing M A, Polisky, B. 1982 *Proc Natl Acad Sci USA.* 79: 3570-3574), (Lin-Chao S, Chen W T, Wong T T. 1992 *Mol. Microbio.* 6: 3385-3393) and runaway replicon R plasmids. Hamann et. al. 2000 (Hamann C W, Nielsen J, Ingerslev E. 2000 World Patent Application WO0028048) report a process for the production of R plasmids wherein plasmid production is maintained at a low level (by use of low temperature) to avoid retardation of growth due to plasmid DNA synthesis; once the host cell population is high, plasmid production is induced by temperature shifting.

Batch Fermentation

Batch fermentation has the main advantage of simplicity. All nutrients that will be utilized for cell growth and plasmid production throughout the culture period are present at the time of inoculation. A batch fermentation has a lag phase, exponential growth phase, and stationary phase. The use of a suitable inoculum (1-5% of the culture volume) will reduce the length of the lag phase. During the exponential phase all nutrients are in excess; thus the specific growth rate will be essentially the maximum specific growth rate, $\mu_{max}$, as predicted by Monod kinetics. As discussed previously, reduced growth rates are desirable for plasmid production. In batch fermentation the growth rate can only be reduced by reducing $\mu_{max}$. This has been achieved by growth at lower temperatures and by growth on glycerol instead of glucose. Batch fermentation at 30° C. using glycerol will typically result in $\mu_{max} \leq 0.3$ h$^{-1}$, which is sufficient to prevent deleterious acetate accumulation and growth rate associated plasmid instability (Thatcher D R, Hitchcock A, Hanak J A J, Varley D L. 2003 U.S. Pat. No. 6,503,738). Glycerol can also be used at much higher concentrations than glucose without being inhibitory, leading to higher biomass yields. Generally, biomass yields of up to 60 g/L DCW can be obtained with batch fermentation.

Fed-Batch Fermentation

Fed-batch fermentation is especially useful for plasmid production. Controlled addition of a limiting nutrient allows for control of growth rate at rates <$\mu_{max}$. Also, fed-batch fermentation results in higher yields. The key to fed-batch fermentation is supplying substrate at a rate such that it is completely consumed. As a result, residual substrate concentration is approximately zero and maximum conversion of substrate is obtained. Metabolic overflow from excess substrate is avoided, reducing the formation of inhibitory acetate.

Fed-batch fermentation starts with a batch phase. Cells are inoculated into an initial volume of medium that contains all non-limiting nutrients and an initial concentration of the limiting substrate. Controlled feeding of the limiting nutrient begins once the cells have consumed the initial amount of substrate.

One of the simplest and most effective feeding strategies is exponential feeding. This method allows the culture to grow at a predetermined rate less than $\mu_{max}$ without the need of feedback control. The fermentation begins with a batch mode containing a non-inhibitory concentration of substrate. The cells grow at $\mu_{max}$ until the substrate is exhausted, at which point the nutrient feeding begins.

The DO-stat and pH-stat methods are fairly easy to implement since most standard fermentor systems include dissolved oxygen and pH monitoring. Trends in dissolved oxygen (DO) and pH can indicate whether substrate is available to the cells. Exhaustion of substrate causes decreased oxygen uptake and the DO concentration in the medium rises. The pH also rises due to consumption of metabolic acids. Feeding is triggered when DO or pH rises above a set threshold. The growth rate can be adjusted by changing the DO or pH threshold value.

Exemplary Plasmid Fermentation Processes

Examination of current yields reveal that typical laboratory shake flask culture produces from 1-5 mg of plasmid DNA/L of culture, whereas a computer controlled fermentor can produce, typically, from 10-250 mg/L.

Lahijani et al. (Lahijani R, Hulley G, Soriano G, Horn N A, Marquet M. 1996 *Human Gene Therapy* 7: 1971-1980) have reported using a pBR322-derived plasmid with a temperature sensitive single point mutation (pUC origin) in a fermentation with exponential feeding and a temperature shift from 37° C. to 42-45° C. They achieved a plasmid yield of 220 mg/L in a 10 L fermentor. The same plasmid without the mutation in batch fermentation (pBR322 derived origin) at 30° C. yielded only 3 mg/L plasmid. Friehs et al. (Friehs K, Flaschel E, Schleef M, Schmidt T. 2003 U.S. Pat. No. 6,664,078) describe a fed-batch process using a glycerol yeast extract medium with DO-stat feedback controlled feeding. The fermentation started with an initial batch volume of 7.5 L. Agitation was increased to keep DO above 30%. Feed medium was pumped in when DO reached a threshold setpoint of 45%. The culture reached stationary phase after 41 hours, yielding 60 g/L DCW and 230 mg/L of plasmid. Chen (Chen, W. 1999 U.S. Pat. No. 5,955,323) used a fed-batch process in semi-defined medium with combination DO-stat and pH-stat feedback control. DO and pH threshold setpoints were 50% and 7.2, respectively. When DO dropped below 30% because of high metabolic activity agitation speed was increased by a percentage of the previous speed. In a 7 L fermentor, this strategy led to a specific growth rate of 0.13 h$^{-1}$ and plasmid yields of 82-98 mg/L. Durland and Eastman, Supra, 1998 report batch fermentation at 37° C. in a proprietary medium. Their process typically yields 130 mg/L and has yielded as high as 250 mg/L.

Even in view of the prior art, there remains a need for a cost effective method for high purity plasmid DNA production. The fermentation media and processes described above incorporate what is currently known in the art to improve plasmid productivity, such as reduced growth rate and plasmid copy number induction with high temperature. These processes plateau at about 200-250 mg plasmid DNA/L. This low yield imposes a cost and purity burden on commercialization of plasmid DNA production processes. Although economies of scale will reduce the cost of DNA significantly in the future, a far more economical solution to this problem is needed in order to achieve the desired cost. As well, international standards for plasmid DNA purity are likely to be the same or very similar to those that are used for recombinant protein products similarly produced from E. coli fermentation, and such standards exceed the current purity attainable from established methods. Increasing the yield (mg of DNA/gram of cell paste) in fermentation would both decrease the cost and increase the purity of the DNA (because it reduces the amount of material being processed).

DISCLOSURE OF THE INVENTION

The invention is a method for production of DNA replicons, utilizing improved batch and fed-batch processes for plasmid production. Specifically, a method of fed-batch fermentation is disclosed in which plasmid-containing E. coli cells are grown at a reduced temperature during the fed-batch phase, during which growth rate is restricted, followed by a temperature up-shift and continued growth at elevated temperature in order to accumulate plasmid, whereby the temperature shift an restricted growth rate improves yield and purity of plasmid. In a preferred embodiment, the reduced growth rate is determined to maintain the plasmid yield below approximately 2 mg/L/OD. In another preferred embodiment, the reduced temperature is around 30° C. In another preferred embodiment, the temperature up-shift is to approximately 36-45° C. In another preferred embodiment, the plasmid contains a ColE1-derived replication origin. In yet another preferred embodiment, the plasmid contains a pMB1 replication origin containing the pUC G to A mutation. In still another preferred embodiment, the plasmid is derived from the VR1012 backbone. In one highly preferred embodiment, the fermentation media is substantially a semi-defined glycerol media. In yet a final preferred embodiment, a pBR322-derived plasmid is grown in E. coli in fed-batch fermentation during which growth rate is restricted during the fed batch phase and growth is continued to accumulate plasmid product. Summarizing, these processes feature high cell density cultivation strategies, combined with novel growth and induction phase temperature shifts. In the production of pBR322-derived origin containing DNA replicons, fed-batch fermentation is performed at restricted cell growth rate. In the production of temperature inducible DNA replicons (e.g. pUC or pMM1 origin containing plasmids) the fed-batch fermentation is performed at restricted cell growth rate and reduced temperature during the growth phase; plasmid production is then induced by temperature up shift. These processes dramatically improve plasmid DNA fermentation yield, while maintaining or improving plasmid integrity, relative to the processes described in the art.

BRIEF SUMMARY OF THE INVENTION

It is a purpose and/or objective of the present invention to provide fermentation processes for the production of plasmid DNA. Another objective and/or purpose of the invention is to improve plasmid DNA production yield in fermentation culture. Yet another objective and/or purpose of the invention is to improve plasmid DNA quality in fermentation culture. Yet another objective and/or purpose of the invention is to reduce impurities in purified plasmid DNA. Another disclosure is improved fermentation processes that, compared to processes defined in the art are improved by: increased yield of plasmid through induction of plasmid levels after biomass production; improved yield and integrity with toxic or unstable plasmids through maintenance of low plasmid levels during biomass production; increased quality of plasmid by reduced levels of nicked (open circular) or linearized versions of the plasmid; increased quality of plasmid by increase in the percent monomer of plasmid; simplified production using robust, automated control parameters and feeds; simplified scaling due to growth control and reduced oxygen supplementation required during growth; reduced levels of impurities after plasmid purification due to enriched levels of plasmid in the feed stream into downstream processing; and improved regulatory compliance by elimination of all animal product derived components.

Further objects and advantages of the invention will become apparent from a consideration of the drawings and ensuing description.

BRIEF DESCRIPTION OF THE DRAWING FIGURES

DETAILED DESCRIPTION OF THE INVENTION

Figure 1A:
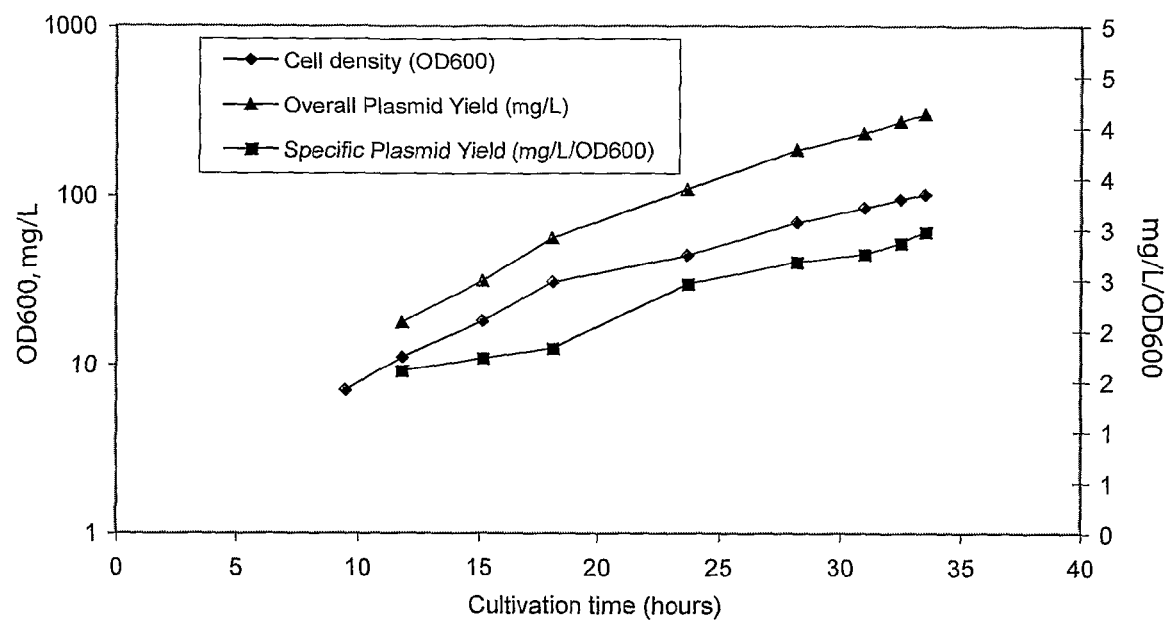
FIG. 1 shows a pBR322-derived plasmid fed-batch fermentation in E. coli with NTC3019 media.
Figure 1B:

Turning now to the drawings, FIG. 1. shows a pBR322-derived plasmid fed-batch fermentation in E. coli with NTC3019 media, revealing: (a) typical growth and plasmid productivity profile of pBR322-derived plasmids in E. coli during fed-batch fermentation with NTC3019 media; and (b) plasmid DNA produced by the NTC3019 media fed-batch fermentation process is highly super-coiled and free of nicked and open circle isoforms.

Figure 2:
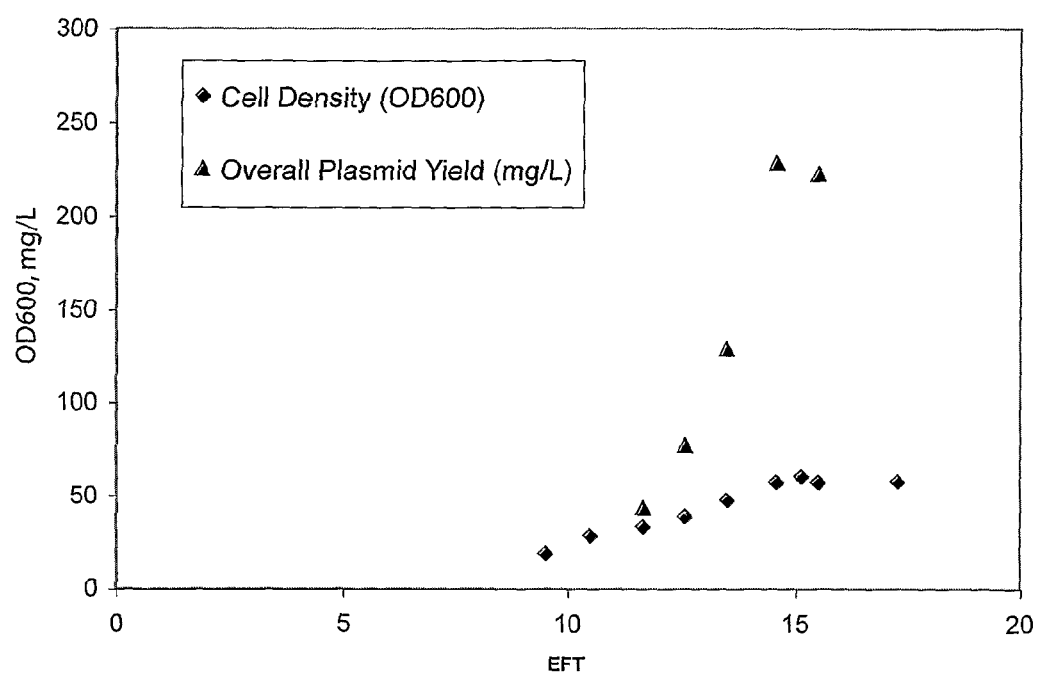
FIG. 2 shows a pUC plasmid batch fermentation in E. coli with NTC3018 media.

In FIG. 2., the plasmid growth and productivity profile of a pUC plasmid (pW2.0) batch fermentation in E. coli with NTC3018 media is shown. The pW2.0 plasmid in batch fermentation reached a cell density of 57 OD600 and yielded 230 mg plasmid/L.

In FIG. 3., a gWiz GFP plasmid fed-batch fermentation in E. coli with NTC3019 medium is shown: (a) growth and control parameter profile (dissolved oxygen, temperature, agitation) of a fed-batch fermentation profile of gWiz GFP; (b) fluorescence microscopy of cells stained with SYBR Green I shows filamentation at the plateau (left), whereas growth resumed and filamentation was reduced after the temperature was reduced to 33° C. (right).

Figure 4:
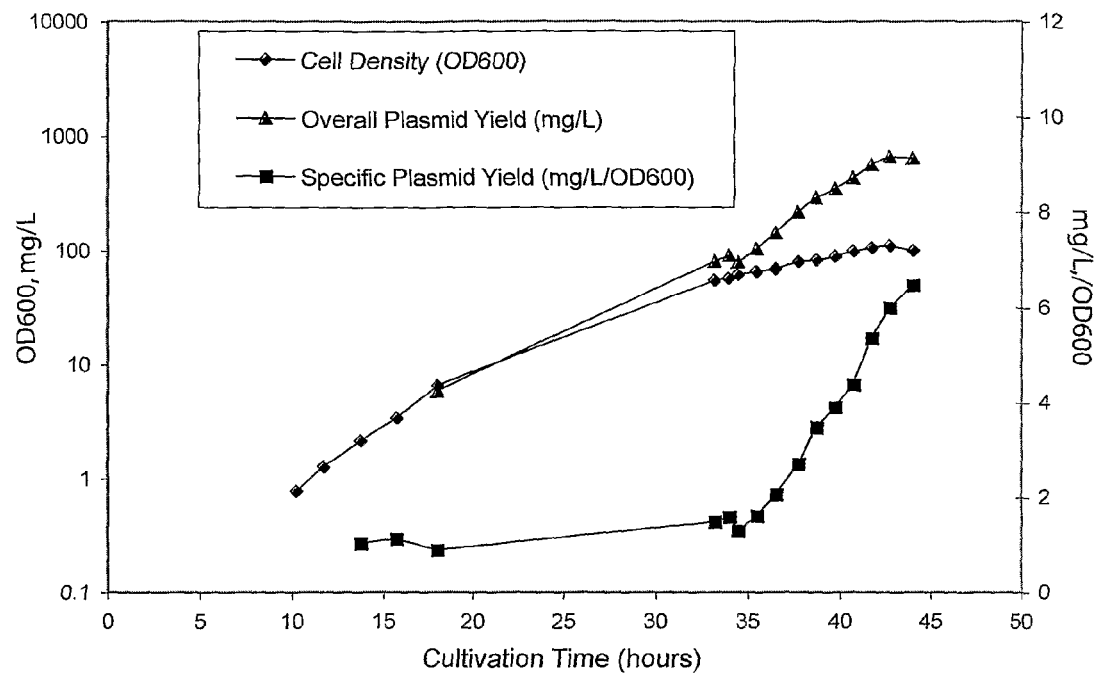
FIG. 4 shows a gWiz GFP inducible fed-batch fermentation in E. coli with NTC3019 medium (37° C. or 42° C. induction).
Figure 4:
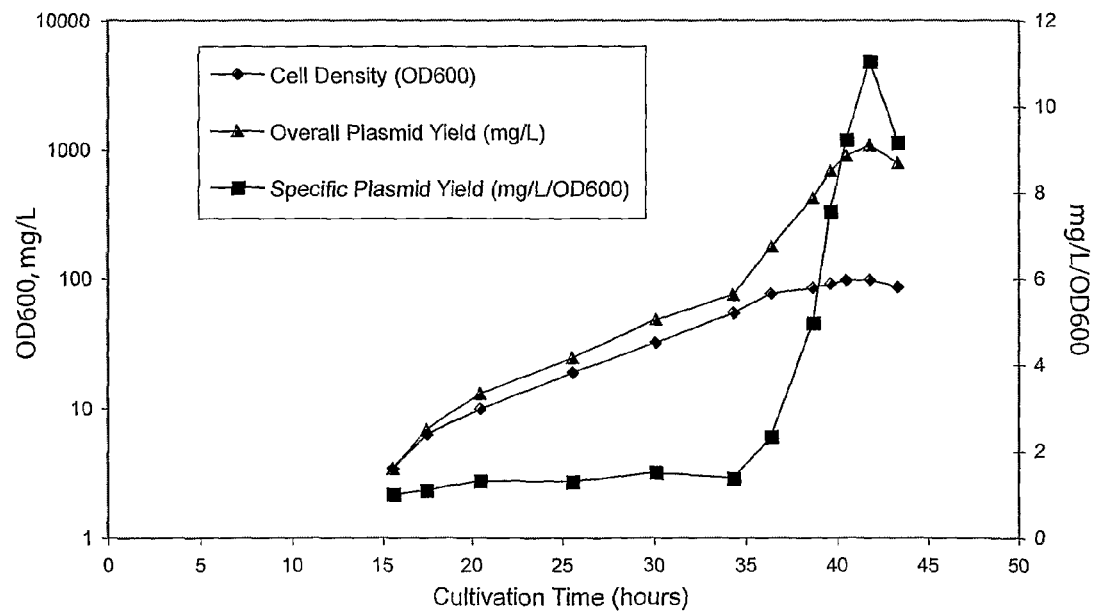

In FIG. 4., a gWiz GFP inducible fed-batch fermentation in E. coli with NTC3019 medium (37° C. or 42° C. induction) is shown: (a) growth and plasmid productivity profile of a gWiz-GFP/E. coli DH5α fermentation with a 30→37° C. temperature shift at 35 hours is revealed, plasmid yield reached 670 mg/L; and (b) growth and plasmid productivity profile of a gWiz-GFP/E. coli DH5α fermentation with a 30→42° C. temperature shift at 35 hours is demonstrated. Plasmid yield reached 1100 mg/L.

Figure 5:
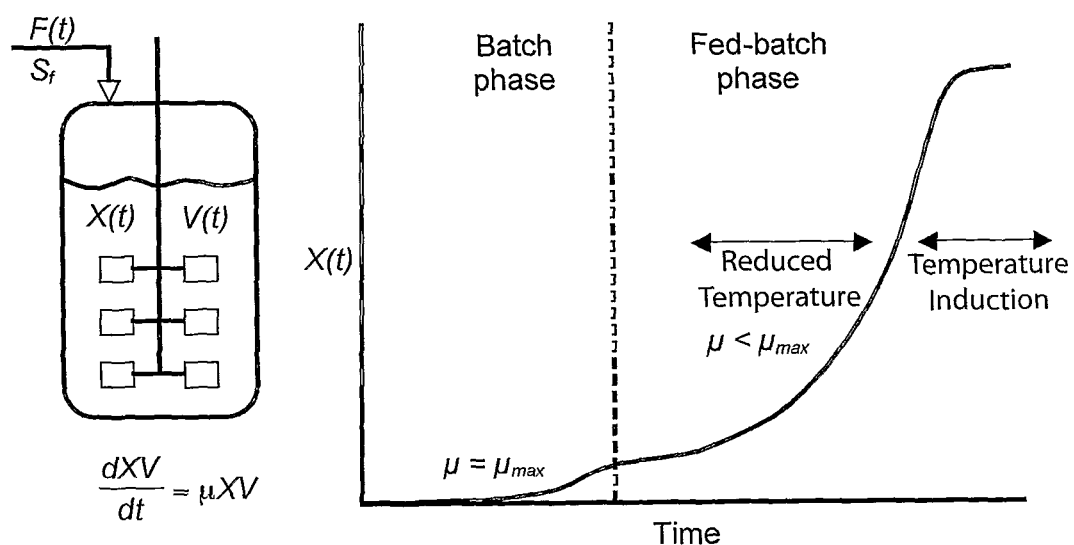
FIG. 5 illustrates an inducible fed-batch fermentation process.

In FIG. 5., the inducible fed-batch fermentation process is illustrated.

Definitions ccc: Covalently Closed Circular

ColE1 derived origin: Origin of replicated derived from ColE1 type plasmid (e.g. pMB1, ColE1) by deletion (e.g. pBR322 derived origin) and/or base change (e.g. pUC from pMB1, pMM1, pMM5 from ColE1 etc)

DNA replicon: plasmids, cosmids, bacterial artificial chromosomes (BACs) bacteriophages, viral vectors and hybrids thereof NTC3018 fermentation media: Glycerol semi defined batch fermentation media NTC3019 fermentation media: Glycerol semi defined fed-batch fermentation media pDNA: Plasmid DNA pBR322-derived origin: pMB1 origin from pBR322, in which the rop (repressor of primer) gene has been deleted plasmid: plasmids, cosmids, bacterial artificial chromosomes (BACs), bacteriophages, viral vectors and hybrids thereof pUC origin: pBR322-derived origin, with G to A transition that increases copy number at elevated temperature semi-defined glycerol media: fermentation media that contains complex nitrogen source (e.g. yeast extract, soy extract) and glycerol carbon source The invention relates to methods for production of covalently closed circular (ccc) recombinant DNA molecules such as plasmids, cosmids, bacterial artificial chromosomes (BACs), bacteriophages, viral vectors and hybrids thereof (herein collectively referred to as plasmids) in a bacterial production host, using a mechanical fermentation vessel.

Fermentation processes described in the art are not optimal, with suboptimal plasmid yield, quality (e.g. nicking or linearization of plasmid), poor scalability (e.g. due to excessive oxygen supplementation requirements), and restricted application (e.g. inability to use with plasmids containing unstable or toxic sequences). The invention is a method for improving yield and purity of plasmid DNA during fermentation culture. A cost effective approach to high yield fermentation has been developed that utilizes an inducible fed batch fermentation process to improve plasmid yield and purity.

Plasmid Production Process and Media Preferred Embodiments

In one preferred embodiment for production of pBR322-derived plasmids, fed-batch fermentation is performed at a restricted cell growth rate. This process dramatically improves plasmid DNA fermentation yield, while maintaining or improving plasmid integrity, relative to the processes described in the art.

Using this process with moderate copy plasmids (e.g. pBR322 replication origin, with ROP gene deleted, herein referred to as pBR322-derived plasmids), plasmid yields of 250-450 mg/L and cell densities of 120 $OD_{600}$ have been achieved with an automated fed-batch fermentation process at 37° C. with feeding controlled to maintain a specific growth rate of $0.12\ hr^{-1}$. This is a 100 fold improvement over reported yields (Lahijani et al., Supra, 1996). The molecular basis for this novel dramatic improvement is unknown. Regardless of the mechanism, application of the invention to production of other plasmids will increase fermentation productivity, without loss of plasmid quality.

In one preferred embodiment for production of temperature inducible DNA replicons (e.g. pUC or pMM1 origin containing plasmids) the fed-batch fermentation is performed at restricted cell growth rate and reduced temperature during the growth phase; plasmid production is then induced by temperature up shift. This process dramatically improves plasmid DNA fermentation yield, while maintaining or improving plasmid integrity, relative to the processes described in the art.

This novel strategy for high yield plasmid production of high-copy origin containing plasmids (e.g. pUC origin) disclosed herein results in unexpected high plasmid productivity and plasmid quality. In addition, growth rate is reduced during the fed-batch phase. The process is shown in FIG. 5. This novel combination of elements has not been applied to the production of ColE1 derived origin plasmids and when tested gave the new and unexpected result of improved productivity. Thus, we teach a new use (improved productivity) for the combination of reduced growth rate with 1) reduced temperature for growth and biomass production, and 2) increased temperature for induction of plasmid production.

The discovery that the combination of an initial reduced temperature growth phase with a later high temperature production phase results in improved overall growth, biomass, and plasmid yield is novel and unexpected, and is not taught in the art. Hamann et al., Supra, 2000 used a temperature inducible fermentation specifically to reduce metabolic burden associated with R plasmids during growth. The strategy was utilized for production of R plasmids, and was not taught for ColE1 origin containing plasmids. As well, Hamann et al., Supra, 2000 does not contemplate improving overall productivity with this strategy. Thus, this combination of elements has not been suggested in the art to improve yield. There is a synergism between the combination which is greater than the sum of the parts as revealed by the improved productivity. As well, the high yield fermentations fill a long felt but unsolved need since the numerous previous processes described in the art over the last 10 years have failed to teach high yield fermentation. In summary, we teach a new combination of elements for ColE1 origin containing plasmid production, comprising slow growth combined with temperature induction that demonstrated the unexpected and surprising new use of improved plasmid productivity.

Application of the inducible fed-batch fermentation process for production of high copy plasmids resulted in yields of 1100 mg/L plasmid DNA, and $OD_{600}$ of 100. This is a five fold improvement over yields obtained with fermentation processes defined in the art. The DNA purified from all these processes is of a high quality, being essentially 100% supercoiled. We contemplate use of the batch and fed-batch fermentation processes described herein to improve plasmid productivity.

The inducible fed-batch process described herein maintained low plasmid levels (<2 mg/L/$OD_{600}$ for VR1012 derived vectors) throughout the biomass production phase of the process, and facilitated unexpected and unprecedented ultra high plasmid production (>6 mg/L/$OD_{600}$ for VR1012 derived vectors) after biomass production. High specific yields are very desirable since increased plasmid yield per gram of bacteria leads directly to higher final product purities. We contemplate utilizing the temperature shift of the invention to keep plasmid levels low (<2 mg/L/$OD_{600}$ for VR1012 derived vectors) throughout growth, inducing plasmid production to high levels (>3 mg/L/$OD_{600}$ for VR1012 derived vectors) after biomass production. These levels are a guideline for production of VR1012 derived vectors. Other plasmids may be tolerated at higher or lower levels than 2 mg/L/$OD_{600}$ during the growth phase. The maximal plasmid level during the growth phase that maintains acceptable metabolic burden, plasmid stability, and enhanced productivity after temperature shift can be determined experimentally for each new plasmid by one of average skill in the art.

Fermentation Media Alternative Embodiments

Exemplary animal product free fermentation media formulations, NTC3018 (batch), NTC3019 (fed-batch) may be utilized in practicing the invention. These media are optimized semi-synthetic growth media, containing glycerol carbon source, yeast extract nitrogen source, and trace metals, salts and buffers. It is anticipated that substitution of this media for those described in the art will also result in improved plasmid productivity using the fermentation processes as described herein.

Alternative non-animal sourced nitrogen sources for use in NTC3018 and NTC3019 media are contemplated. As a complex media component, yeast extract provides nitrogen, amino acids, vitamins, and carbon. Possible components of complex media (e.g. yeast or soy extracts) key to cell metabolism during plasmid production include limiting amino acids, vitamins, trace minerals and alternative carbon sources. By way of example, we contemplate use of alternative yeast extract preparations, soy preparation (e.g. select soytone, or phytone peptone from BD Biosciences) or other vegetable preparations (e.g. pea flower peptones from Oxoid) in NTC3018 and NTC3019 media.

Variations in the defined elements of the media are also contemplated. For example, increased phosphate or magnesium is contemplated, either as increases in the batch media component, or as additions to the feed in fed-batch fermentation. Further optimization of the media, by systematic component evaluation can be performed by one skilled in the art of fermentation.

Additives to the media are contemplated when utilizing certain auxotrophic cell lines. For example, cell lines such as Stbl2 (InVitrogen Corp.) that contain the proAB deletion may need amino acid supplementation, or an alternative nitrogen source rich in proline, to achieve maximal growth. Such modifications can be determined by one of average skill in the art of fermentation.

We also contemplate use of the batch and fed-batch fermentation processes described herein with plasmid fermentation media described in the art. This includes defined media such as those disclosed by Soubrier (Soubrier F. 2004 US Patent application 2004/0142452). Preferred media to use with the fed-batch fermentation processes of the invention are glycerol media formulations with semi-defined feeds, such as NTC3019 and those disclosed in Lahijani et al., Supra, 1996, Friehs et al., Supra, 2003, Chen Supra, 1999. and Urthaler et al. (Urthaler J, Roman N, Ascher C, Woehrer H.2005 US Patent Application 2005/0026177).

Fermentation Process Alternative Embodiments

Improved fed-batch and batch processes for plasmid production are disclosed herein. These feature exponential feed strategies, combined with novel growth and induction phase temperature shifts.

In practicing the fed-batch processes of the invention, we contemplate various feeding strategies to reduce growth rate, including feedback, feed-forward, and predetermined control of nutrient feeding. For example, nutrient feed may be added according to a carbon limiting exponential feeding strategy. We anticipate variation of this feeding strategy to control growth rate within acceptable ranges. Preferred growth rate ranges are $\mu=0.05$ to $0.3\ hr^{-1}$. A preferred target growth rate is $\mu=0.12\ h^{-1}$. Acceptable growth rate ranges will be plasmid specific and can be determined experimentally by those skilled in the art.

In practicing the fed-batch processes of the invention, we contemplate various batching strategies to reduce production time. The semi-defined nutrient included in the batch phase can be adjusted, to allow the batch phase to proceed to higher or biomass concentrations. In the case of higher biomass concentration, overall fermentation time is reduced since growth is faster in the batch phase compared to the fed-batch phase. We anticipate variation of this batching strategy to control the start of the fed-batch phase of the process. Preferred $OD_{600}$ ranges for the fed-batch phase to start are from 1 to 60. Acceptable fed-batch starting $OD_{600}$ ranges may be plasmid specific and can be determined experimentally by those skilled in the art.

In practicing the inducible fed-batch and batch processes of the invention, we contemplate various temperature shifting strategies from the growth to the induction phase. The growth phase can be performed at temperatures from 25-37° C., preferably at 30-37° C. For high copy plasmids, the growth phase is most preferably 30-32° C. The induction phase can be performed at temperatures from 33-45° C., and preferably 37-42° C.

In practicing the inducible processes with temperature shifting strategies, we contemplate using nutrient concentration, biomass concentration, or optical density as an indicator of when to switch from the growth phase to the induction phase. Regular sampling of the fermentation culture can provide material to obtain biomass or optical density measurements and the temperature shift can be performed at a certain biomass concentration. Online sensors can also be used to provide continuous monitoring of biomass concentration and the fermentor can be set to automatically perform the temperature shift at a specified biomass concentration. In practicing the inducible fed-batch process with temperature shifting strategies we also contemplate performing the temperature shift once a certain amount of feed nutrient has been added.

In practicing the inducible processes with temperature shifting strategies, we contemplate using higher temperatures during the growth phase to minimize production times. The inducible fed-batch process described herein maintained low (<2 $mg/L/OD_{600}$) plasmid levels throughout the growth phase of the process. The maximal temperature that can be utilized during the growth phase that maintains acceptable metabolic burden, plasmid stability, and enhanced productivity after temperature shift will be plasmid specific and will vary between different plasmid backbones. For example, some plasmids may be tolerated at much higher levels than 2 $mg/L/OD_{600}$. As well, plasmid productivity may vary at low temperature, such that some plasmids may not produce as high levels of plasmid. In these cases, we contemplate using higher temperatures during the growth phase. Additionally, increased maximal temperatures may be tolerated during the initial batch phase due to unrestricted growth and corresponding lower plasmid copy numbers (FIG. 5). The maximal temperature that can be utilized during the growth phase (batch and fed-batch components), that maintains acceptable metabolic burden, plasmid stability, and enhanced productivity after temperature shift can be determined experimentally by one of average skill in the art.

Plasmids and Host Strains

We contemplate use of the invention in the production of plasmids with a variety of origins of replication, that are either high copy, low copy and moderate copy, and are either temperature inducible or not. Some preferred origins of replication, and plasmids incorporating them, are outlined in Table 1. Modifications to these origins are known in the art, and are also contemplated for use.

TABLE 1

Replication origins

| Parent Origin | Regulation | High copy Derivation | Copy Number | Therapeutic plasmids |
|---|---|---|---|---|
| pMB1 | Antisense RNAI binds RNAII. Rop accessory protein stabilizes interaction | pUG origin (Rop deletion and second site mutation that alters RNAI/II interaction at 37 and 42, not 30 C.) | 50 at 37° C., 175 at 42° C. (log phase) | Multiple (pcDNA3, pVAX, VR1012, etc) |
| | | pUC origin with second site enhancer increases copy number 14-50% | Not determined | pDNAVACCultra |
| | | Rop deletion | 30 at 37° C. and 42° C. (log phase) | pCMVKm2 |
| | | G to T mutation (extends RNAI, attenuating repressor; not conditional) Plasmid is 65% total DNA | 1000 (phase not indicated) | Not described |
| ColEI | Same as pMB1 | pMM1, pMM7 (Rop deletion and second site mutation that alters RNAI/RNAII interaction at 37 and 42, not 30 C.). pMM7 is >50% total DNA in stationary phase | 2000 in stationary phase (pMM7) | pVC0396† |
| R6K (ori α, ori β, ori γ) | π rep protein binds iteron, copy number dependent activation (low) or repression (high) | Host strain pir-116 mutant (π rep protein copy-up mutation in oligomerization domain removed from plasmid and provided in trans from chromosome) | 200 250 | pCpG, pBoost pCOR |
| R1 | RepA initiator protein binds non repeated target. Antisense CopA repressor binds RepA leader (CopT). Auxiliary CopB protein represses RepA expression. | Temperature inducible copy number using dual origin mutant (plasmid is 75% total DNA) | 2000 (mutant) | Not described |
| | | RepA controlled by temperature inducible lambda $P_R$ promoter and temperature sensitive lambda repressor controlled. (Plasmid is 50% total DNA) | 1000 ($P_R$ controlled) | pCWH24-6 |
| pKL1 | Rep A initiator protein represses repA on transcription as hexamer | Rep A initiator protein overexpression separate plasmid or on chromosome | >2500 | Not described |

†pVC0396 is an optimized vector backbone, for insertion of eukaryotic expression cassettes Alternative host strains are contemplated. *E. coli* strain DH5α is a widely used host for plasmid production. Its key qualities include the recA mutation, which minimizes non-specific recombination of cloned DNA, and the endA1 mutation, eliminating non-specific digestion of plasmid by Endonuclease I. In addition to DH5α, a variety of other strains are suited for plasmid production; a non limiting list of exemplary *E. coli* host strains is shown in Table 2.

TABLE 2

Host strains

| Strain | Genotype | Source |
|---|---|---|
| DH1 | recA1 endA1 hscR17(rk−, mk+) phoA supE44 λ-thi-1 gyrA96 relA1 | Invitrogen |
| DH5α | F− Φ80dlacZΔM15 Δ(lacZYA-argF) U169 recA1 endA1 hsdR17(rk−, mk+) phoA supE44 λ-thi-1 gyrA96 relA1 | |
| DH10B | F− mcrA Δ(mrr-shdRMS-mrcBC), Φ80dlacZΔM15 ΔlacZ74, deoR, recA1, endA1, araD139, Δ(ara-leu)7697, galU, galK, λ,-rpsL, nupG | Invitrogen |
| JM109 | endA1, recA1 gyrA96, thi, hsdR17(rk−, mk+) relA1, supE44 λ− Δ(lac-ProAB) [F′traD36, proAB lacI$^q$ZΔM15] | Stratagene |
| XL1-Blue | recA1 endA1 gyrA96 thi-1 hsdR17 supE44 relA1 lac [F′proAB lacI$^q$ZΔM15 Tn10 (Tet$^r$)] | Stratagene |
| Top10 | F− mcrA Δ(mrr-hsdRMS-mcrBC) Φ80lacZΔM15 ΔlacX74 recA1 araΔ139 Δ(ara-leu)7697 galU galK rpsL (Str$^R$) endA1 nupG | Invitrogen |
| Mach1 | ΔrecA1398 endA1 tonA Φ80ΔlacM15 ΔlacX74 hsdR(r$_k^−$m$_k^+$) | Invitrogen |
| GT116 | F− mcrA Δ(mrr-hsdRMS-mcrBS) Φ80lacZΔM15 ΔlacX74 recA1 endA1 Δdcm ΔsbcC-sbcD | Invivogen |
| ECOS101 | F− (Φ80 ΔlacZ ΔM15)Δ(lacZYA-argF)U169 hsdR17(r$_{K−}$ m$_{K+}$) recA1 endA1 relA1 deoR λ− | Yeastern |
| EC100 | F− mcrA Δ(mrr-hsdRMS-mcrBS,) Φ80 ΔlacZ ΔM15)ΔlacX74 recA1 endA1 araD139(ara, leu)7697, galU, galK, λ− rpsL, nupG | Epicentre |
| Sure | e14− (McrA−) Δ (mcrCB-hsdSMR-mrr)171 endA1 supE44 thi-1 gyrA96 relA1 lac recB recJ sbcC umuC::Tn5 (Kan$^r$) uvrC [F′ proAB lacI$^q$Z□M15 Tn10 (Tet$^r$)] | Stratagene |
| Stb12 | F− mcrA Δ(mcrBC-hsdRMS-mrr) recA1 endA1 Ion gyrA96 thi supE44 relA1 λ− Δ(lac-proAB) | Invitrogen |
| Stb14 | mcrA Δ(mcrBC-hsdRMS-mrr) recA1 endA1 gyrA96 gal− thi-1 supE44 λ− relA1 Δ(lac-proAB)/ F′ proAB+ lacI$^q$ZΔM15 Tn10 Tet$^R$ | Invitrogen |

DH5α, XL1-Blue, DH10B, JM109 and Top 10 have been well established as plasmid production strains. Mach1, and ECOS101 have been developed recently and may be desirable plasmid production hosts. Stb12, GT116 and Sure cells have been utilized for the production of unstable DNA containing plasmids. Unstable DNA contains structures like direct (e.g. retroviral long terminal repeats) or inverted repeats (e.g. shRNA palindromes), Z DNA, etc. The deletion of the dcm gene in GT116 eliminates dam methylation which is immuno-stimulatory. Therefore, production in GT116 reduces the immunogenicity of plasmid DNA. Similar reductions in immunogenicity are observed utilizing strains expressing CpG methylase.

Production of Unstable Plasmids

We also contemplate use of the invention in the production of plasmids containing unstable sequences. Palindrome sequences, direct or inverted repeats, and Z DNA forming sequences are unstable and are deleted or rearranged by *E. coli* hosts. In some instances, plasmids for therapeutic use must contain unstable sequences (inverted or direct repeats for viral vectors such as AAV and HIV, Z DNA forming segments or triplet repeats for certain therapeutic genes). Current strategies to maintain plasmids containing unstable sequences are to use host cell lines with stabilizing mutations. Several hosts are commercially available for propagation of these plasmids, for example, Sure cells (Stratagene), GT115 (Invivogen) or Stb12 and Stb14 (Invitrogen). The Stb12 and Stb14 cell lines utilize an undisclosed mutation that increases stability of direct repeat containing vectors such as retroviral vectors; this effect is enhanced at reduced temperature, presumably due to reduced copy number. Specific combinations of repair mutations can stabilize plasmid propagation, especially at low temperature. The Sure and Sure2 cell lines uses one such combination, with homologous recombination deficiency (recB, recJ) in conjunction with IV repair (uvrC) and SOS repair (umuC) deficiency (to stabilize LTRs), and SbcC (and recJ) to stabilize Z DNA. The GT116 cell line uses SbcC and SbcD to stabilize palindromic sequences. These strains function to stabilize plasmids only at low temperature (i.e. 30° C.), presumably due to reduced plasmid copy number. This strategy obviously increases production cost. Use of the inducible fermentation process described herein would allow propagation at 30° C. of unstable plasmids in stabilizing cell lines, prior to increasing copy number only for a short duration prior to harvest. This should maximize yield and stability (i.e. quality) of unstable plasmids.

DNA and Plasmid Production

The underlying mechanism for the observed increased yield of plasmid DNA (>6 mg/L/OD$_{600}$) in the inducible fed-batch process is unknown. It is potentially due to induction of DNA compaction agents (e.g. histone-like protein or other chromatin binding proteins, such as the dps gene product) during biomass production at slow growth and reduced temperature.

Altering DNA condensation during the induction phase may increase plasmid yield by increasing tolerable plasmid levels or copy number. The degree of compaction of a DNA is set by two opposing factors; condensing chromatin proteins and decondensing transcription complexes. Plasmid compaction may be affected by the level of transcription from plasmid promoters. Less transcription may be associated with higher compaction, and potentially higher carrying capacity.

In *E. coli*, a number of chromatin proteins have been identified that are involved in DNA compaction. These gene products bind plasmid and genomic DNA. In the case of genomic DNA, they compact the DNA into the nucleoid (reviewed in (Robinow C, Kellenberger E. 1994 *Microbiol Review* 58: 211-232)). The major components of the nucleoid are the histone like proteins HU, IHF, and HN-S, StpA (related to HN-S, expressed at about 1/10 level) and Dps, which are distributed uniformly in the nucleoid, while other proteins, such as SeqA, CbpA, CbpB, Fis and IciA are in lower amount, show non-uniform distribution in the nucleoid, and may have regulatory functions. An isolated R plasmid protein complex contained three major proteins, 23% HN-S, 23% RNA polymerase, and 5% HU. This would presumably change depending on growth phase since chromatin associated gene products are differentially regulated in different media, different cell densities and during growth and stationary phases. Fis, HU, HF-1 generally are more highly expressed in log phase, while IHF and Dps are at higher levels in stationary phase. Dps condenses DNA into liquid biocrystalline complexes in stationary phase to improve stress resistance. Over-expression of HN-S during the growth phase leads to DNA condensation and viability loss. Cells may have higher plasmid capacity when DNA is highly compacted. In the NTC inducible fermentation process, growth phase cells have lower overall capacity for plasmid DNA than induction phase cells. This may be due to differences in the combinations of chromatin proteins present in the induction phase which may allow higher levels of tolerable plasmid than in the growth phase. Alternations to the ratios of chromatin proteins during the induction phase may increase plasmid compaction, and carrying capacity.

Alternations to the ratios of chromatin proteins during the induction phase may also increase plasmid replication rates. For example, expression from the p15A origin RNAII promoter, but not the pMB1 (pBR322) RNAII promoter, is repressed by IHF; p15A RNAII transcription is increased in IHF mutants. Dps and HU are non-specific DNA binders, HN-S, CbpA and CbpB bind curved DNA. StpA is related to HN-S, binds DNA with higher affinity, and also binds curved DNA. Fis, IHF, IciA and seqA are sequence specific. HN-S represses transcription from a number of promoters that contain curved DNA. The RNAII promoter of pMB1 (pUC and pBR322) contains polyA and poly T tracks; these sequences form curved DNA. The decreased levels of curved DNA binding chromatin proteins that repress transcription (e.g. HN-S) in stationary phase may be associated with increased ratio of RNAII to RNAI transcription, and the documented stationary phase increase in plasmid copy number. Alterations to the composition of the chromatin proteins (e.g. further decrease in HN-S) present during the production phase of NTC fermentation process may lead to increased plasmid copy number with pMB1 plasmids such as pUC.

Heterologous DNA compactors, for example, the acid soluble spore proteins of *Bacillus* species, when expressed in *E. coli*, may also be useful DNA compactors for increasing plasmid yield. For example, expression of a *B. subtilis* small acid soluble protein in *E. coli* causes DNA (Setlow B. H and A R, and Setlow P. *J. Bacteriol.* 173: 1642-1653).

Process alterations may also improve yields through effects on DNA condensation. Dps is regulated by Magnesium (Mg$^{++}$) concentration; the presence of Dps does not result in DNA condensation; tightly packed crystalline DNA: Dps complexes form when Mg$^{++}$ concentration falls below a threshold [reviewed in (Frenkiel-Krispin D, Levin-Zaidman S, Shimoni E, Wolf S G, Wachtel E J, Arad T, Finkel S E, Kolter R, Minsky A. 2001 *EMBO J.* 20: 1184-1191)]. Morphologically, the complex resembles that induced by chloramphenicol addition during stationary phase. Addition of 0.2 mM spermidine to growing cultures accelerates DNA condensation in the absence of Dps. Phosphate starvation has the same effect, perhaps through enhanced degradation of threonine and arginine to spermidine (Frenkiel-Krispin et al., Supra, 2001). Changes to fermentation composition or conditions during the induction phase, to alter the levels of divalent cations (e.g. Mg$^{++}$, through exogenous addition or depletion), or alter the level of positively charged polyamines (e.g. spermidine, through exogenous addition or control of bacterial synthesis) may increase plasmid yield and are contemplated as alterations to the media.

We contemplate further yield increases may be obtained by further compaction of plasmid DNA. This could be achieved by addition of DNA compaction agents to the feed (e.g. polyethyleneimine, spermidine, spermine) or strain modifications that increase production of host strain DNA compaction agents such as spermine production or dps protein production, during the fermentation process. Such strain modifications could be alterations that allow the relevant gene products to be induced during the fermentation process.

In practicing the inducible processes, we contemplate using alternative strategies to maintain plasmid copy number at a low level during the growth phase. For example, in addition to growth at a low temperature, other mechanisms exist to reduce copy number that could be incorporated into the growth phase. For example, reduced dissolved oxygen during fermentation has been shown to reduce plasmid copy number (Carnes A E, 2005 *BioProcess International* 3:9, in press).
Improvement to Final Product Purity We contemplate utilizing plasmid enriched feed streams from the described fermentation culture in exemplary plasmid purification processes. Such processes are well known in the art. The combination of high yield fermentation and exemplary purification process may provide cost effective methodologies to further reduce genomic DNA to acceptable levels for gene therapy and DNA vaccination applications.

EXAMPLES

The method of the invention is further illustrated in the following examples. These are provided by way of illustration and are not intended in any way to limit the scope of the invention.

Example 1

NTC3018 and NTC3019 Fermentation Media

The following criteria were established for evaluation of an optimized fermentation process for manufacturing plasmid DNA:
1) High specific yield of plasmid (mg plasmid DNA per g cell mass);
2) High biomass yield;
3) It will retain high degrees of super-coiled plasmid;
4) It will cause minimal problems during downstream processing;
5) It will meet regulatory requirements; and
6) It will retain plasmid structure (e.g. no deletions or other rearrangements).

Culture media was formulated to support high specific plasmid yield, high biomass yield, and high plasmid quality. The batch fermentation medium was designed to reduce the specific growth rate. The use of a reduced growth rate has been associated with higher plasmid copy number and better plasmid stability. During fed-batch fermentations the growth rate was controlled at 0.12 $h^{-1}$ by feeding of the limiting nutrient. The host strain, DH5α, has the endA1, recA, and relA mutations, all important for plasmid production. Additionally, all components used in the media were well characterized and certified animal product free.

NTC3018 (batch) and NTC3019 (fed-batch) media are optimized for many components of both batch and fed-batch process media. For example glycerol is utilized as the carbon source rather than glucose to reduce the growth rate. Yeast extract is used as the nitrogen source. The trace metals and $MgSO_4$ concentrations have been optimized, based on determined requirements of *E. coli* production strains.

Example 2

NTC3019 Media Fed-Batch Culture with pBR322-Derived Plasmids

Fed-batch fermentations were carried out in a New Brunswick BioFlo 110 fermentor at 37° C. pH was controlled by automatic addition of 30% ammonium hydroxide or 10% phosphoric acid. The dissolved oxygen probe was calibrated to 0% by nitrogen gas sparging and 100% with air saturation. The vessel was aerated at IVVM and dissolved oxygen was maintained at 30% by proportional-integral control of agitation. At cell densities above about 20 $OD_{600}$, $O_2$ supplementation was also required to maintain 30% saturation.

Seed cultures were started from single isolated colonies inoculated into LB plus 50 μg/ml kanamycin and grown at 37° C. At mid-exponential phase (0.5-1.5 $OD_{600}$) the seed cultures were used to provide 1% inoculums for the fermentor.

During fed-batch cultures a semi-defined feed nutrient was added according to a carbon limiting exponential feeding strategy. Briefly, an initial amount of carbon substrate is consumed during the batch phase at a specific growth rate of $\mu_{max}$. Upon exhaustion of the carbon substrate, the fed-batch phase begins and feed nutrient is added automatically at the rate determined by the following equation (Carnes, Supra, 2005):

$$F(t) = \frac{\mu X_B V_B}{S_f Y_{X/S}} e^{\mu t}$$

Where μ=desired specific growth rate during fed-batch phase,
$X_B$=biomass concentration at the end of the batch phase, g DCW/L,
$V_B$=initial liquid volume of culture, L,
$S_f$=limiting substrate concentration in nutrient feed medium, g/L,
$Y_{X/S}$=yield coefficient of biomass from substrate, g/g,
t=time since beginning of fed-batch phase.

Typically, fed-batch fermentations in NTC3019 media with several independent kanamycin resistant pBR322-derived plasmids reach a cell density of 100-120 $OD_{600}$, or 55-65 g dry cell weight per liter (FIG. 1). Plasmid yields average 260 mg/L and have been as high as 430 mg/L. By comparison, published fermentation yields with pBR322-derived plasmids are on the order of 3-4 mg/L (Lahijani et al., Supra, 1996).

Importantly, the specific plasmid yields are very high, typically between 2.5 and 3.8 mg/L/$OD_{600}$, well exceeding levels observed with other fermentation media/processes using much higher copy pUC origin plasmids (Table 3). Expressing plasmid yields in terms of specific yields mg/L/$OD_{600}$ indicates the amount of plasmid relative to the total cell mass. High specific yields are very desirable since increased plasmid yield per gram of bacteria leads directly to higher final product purities.

TABLE 3

Comparison of specific plasmid yields with published high yield fermentation processes

| Fermentation process | Specific plasmid yield, mg/L/$OD_{600}$ |
|---|---|
| Friehs et al., Supra, 2003 (fed-batch) | 1.3-2.1 |
| Lahijani et al., Supra, 1996 (fed-batch) | 2.8 |
| NTC3019 pBR322-derived origin fed-batch (Example 2) | 2.5-3.8 |
| NTC3018 pUG origin batch (Example 3) | 2.9-5.3 |
| NTC3019 pUC origin fed-batch (Example 4) | 2.7 |
| NTC3019 pUG origin inducible fed-batch (Example 5) | 6.5-11 |

This demonstrates that NTC3019 fermentation media dramatically boosts the fermentation yields of moderate-copy number plasmids (e.g. pBR322 with rop deletion) relative to media and processes described in the art. This effect is not plasmid specific.

The DNA purified from these processes is of a high quality, being essentially 100% super-coiled with no detectable deletion or other rearrangement. As well, DNA purifications at the 1 gram scale have been performed utilizing the cells from this process. This demonstrates fermentations performed in NTC3019 fed-batch media are amenable to large scale downstream processing.

Example 3

NTC3018 Medium Batch Fermentation with High-Copy Gene Therapy Plasmid

NTC3018 medium batch culture with pUC origin plasmids was performed. The following pUC origin containing plasmids were utilized:
1) pW2.0, a derivative of pUC19 that has an altered polylinker sequence.
2) pMaxGFP
3) pEGFP-C1

Batch fermentations were carried out in a New Brunswick BioFlo 110 fermentor at 37° C. pH was controlled by automatic addition of 30% ammonium hydroxide or 10% phosphoric acid. The dissolved oxygen probe was calibrated to 0% by nitrogen gas sparging and 100% with air saturation. The vessel was aerated at 1VVM and dissolved oxygen was maintained at 30% by proportional-integral control of agitation. At cell densities above about 20 $OD_{600}$, $O_2$ supplementation was also required to maintain 30% saturation.

Seed cultures were started from single isolated colonies inoculated into LB plus 50 µg/ml kanamycin or 100 µg/ml ampicillin and grown at 37° C. At mid-exponential phase (0.5-1.5 $OD_{600}$) the seed cultures were used to provide 1% inoculums for the fermentor.

All fermentations were performed at 37° C. For pW2.0, plasmid copy number was induced by growth at 42° C. late in the fermentation. Batch fermentations with pUC plasmids reached cell densities of only 16-57 $OD_{600}$. However, specific plasmid yield results are encouraging. Final yields for pEGFP-C1 were a cell density of 56 $OD_{600}$ and yielded 163 mg plasmid/L (2.9 mg/L/$OD_{600}$), pMaxGFP a cell density of 16 $OD_{600}$ and yielded 84 mg plasmid/L (5.3 mg/L/$OD_{600}$) and for pW2.0 a cell density of 57 $OD_{600}$ and yielded 230 mg plasmid/L (4.0 mg/L/$OD_{600}$; FIG. 2).

The DNA purified from these processes is of a high quality, being essentially 100% super-coiled with no detectable deletion or other rearrangement. As well, DNA purifications at the 0.5 gram scale have been performed utilizing the cells from this process. This demonstrates fermentations performed in NTC3018 batch medium are amenable to large scale downstream processing.

Example 4

NTC3019 Media Fed-Batch Fermentation with High-Copy Gene Therapy Plasmids

The plasmid gWiz GFP (Gene Therapy Systems) which is a GFP gene containing derivative of the Vical VR1012 vector was selected for fed-batch fermentation evaluation. This is a widely used kanamycin resistance (kanR) pUC origin containing DNA vaccine plasmid with a size of 5757 bp. The plasmid gWiz GFP (Gene Therapy Systems) was transformed into *E. coli* DH5α. pMaxGFP was also tested in fed-batch cultures; similar results were obtained for both plasmids.

Figure 3A:
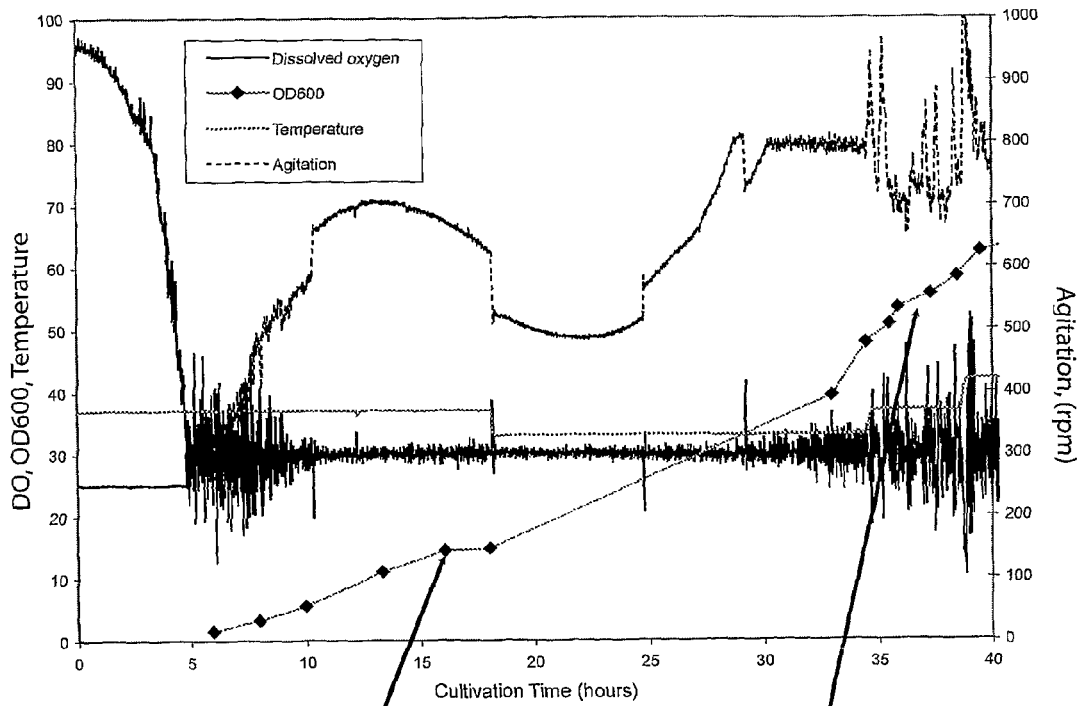
FIG. 3 shows a gWiz GFP plasmid fed-batch fermentation in E. coli with NTC3019 medium.

Two problems were encountered when using NTC3019 media for producing these plasmids. The first problem was discovered when growing gWiz GFP plasmid cultures at 37° C., as was done successfully with the pBR322-derived plasmids. With the pUC plasmid cultures, cell growth stopped around 15 $OD_{600}$. Fluorescence microscopy showed extensive filamentation, indicating inhibition of cell division. This is lethal, since the filaments eventually lyse (Arends S J R, Weiss, D S. 2004 *J Bacteriol* 186: 880-884). For example, FIG. 3(A) shows fed-batch fermentation with the plasmid gWiz GFP. Cell growth had slowed and appeared to be entering stationary phase prematurely at 15 $OD_{600}$. Plasmid yield analysis indicated an elevated specific plasmid yield of 2.7 mg/L/$OD_{600}$ as the cell growth began to stop. pUC plasmids contain a temperature sensitive point mutation that can exhibit a 30-40 fold increase in copy number at 42° C. when compared to 30° C. (Lin-Chao et al., 1992). The temperature was then reduced to 33° C. in an attempt to reduce the plasmid copy number and thus alleviate the metabolic burden on the cells, after which the plasmid dropped to 1.6 mg/L/$OD_{600}$ and cell growth resumed. Interestingly, the specific plasmid yield gradually rose again and growth entered stationary phase at about 60 $OD_{600}$ instead of growing to >100 $OD_{600}$ as expected, even though feed nutrient was still being added.

Figure 3B:

FIG. 3(B) shows cell filamentation that had occurred at 37° C. After the temperature was reduced to 33° C., a sample of growing cells showed much less filamentation.

A possible explanation was that the cell population never fully recovered from the filamentation and loss of viability when begun at 37° C. To test this, two subsequent fed-batch fermentations with the same plasmid were carried out entirely at 33° C. In both fermentations, the culture peaked at cell densities <60 $OD_{600}$.

Biomass and plasmid DNA yield data from these fermentations indicate a reduction in specific growth rate and a sharp rise in specific plasmid yield before inhibition of cell growth. The sudden rise in plasmid content to such a high level was unexpected, and places a metabolic burden on the cell population, which may be the cause of the reduced growth rate. However, it has also been shown that reductions in growth rate often lead to an increase in plasmid copy number (Satyagal V N, Agrawal P. 1989 *Biotechnol. Bioeng.* 33: 1135-1144), (Seo J H, Bailey J E. 1985 *Biotechnol. Bioeng.* 27: 1668-1674). It is unclear whether the unexpected increased specific plasmid yield is causing the reduced growth rate, vice versa, or whether each is causing the other in a compounded manner.

Example 5

Inducible Fed-Batch Process for High Yield Production of High Copy Plasmids with NTC3019 Media Based on the results from the 33° C. and 37° C. fermentations (Example 5), a strategy was designed to overcome the unexpected plasmid increase observed in fed-batch mode with pUC origin plasmids. The plasmid gWiz GFP in DH5α was utilized in an inducible fed-batch process. NTC3019 fed-batch fermentation was performed as outlined in Example 5, except the culture was grown at 30° C. until 60 $OD_{600}$, at which time the temperature was shifted to 37° C. The surprising results are shown in FIG. 4A. Growth at 30° C. through 60 $OD_{600}$ eliminated the growth arrest problem, and the culture ultimately exceeded 100 $OD_{600}$ with a total plasmid yield of 670 mg/L. The DNA purified from samples from this process is of a high quality, being essentially 100% supercoiled with no detectable deletion or other rearrangement.

Plasmid yields prior to the temperature shift remained low throughout the growth phase, remaining below 2 mg/L/$OD_{600}$. This is in contrast to the results from 33° C. or 37° C. fermentations. Remarkably, the specific plasmid yields after temperature shift are very high, up to 6.5 mg/L/$OD_{600}$, well exceeding levels observed with other fermentation media/processes (Table 3). Fermentation at 30° C. through the growth phase, and shifting to 42° C. resulted in productivity yields of 1.1 gm/L (11 mg/L/$OD_{600}$) with gWiz GFP (FIG. 4B). Productivity plateau is not associated with extensive cell death, as the majority of the cells remain viable.

Modification of the NTC3019 media (four fold increase in glycerol, yeast extract, and magnesium in the batched media) to reduce the duration of the fed-batch phase (by extending the batch phase to higher $OD_{600}$) also produced similarly high plasmid yields after induction at 42° C., demonstrating that the fed-batch phase can be started at higher $OD_{600}$ without loss of plasmid induction.

Multiple different plasmids with various pUC origin backbones, including different antibiotic resistance genes and orientations of prokaryotic elements, have been produced in yields greater than 0.5 gm/L in NTC3019 media, using the 30° C. to 42° C. inducible process in DH5α. These results demonstrate that the inducible process is not specific to a particular plasmid.

The gWiz-GFP plasmid was also produced in yields greater than 500 mg/L in NTC3019 media, using the 30° C. to 42° C. inducible process, in the DH1 cell line. This result demonstrates that the inducible process is not specific to a particular E. coli strain.

As well, DNA purifications at the 1 gram scale have been performed utilizing the cells from this process. This demonstrates inducible fermentations performed in NTC3019 fed-batch media are amenable to large scale downstream processing.

Expressing plasmid yields in terms of specific yields (mg/L/$OD_{600}$) indicates the amount of plasmid relative to the total cell mass. The inducible fed-batch process described herein maintained low (<2 mg/L/$OD_{600}$) plasmid levels throughout the growth phase of the process, and facilitated unprecedented ultra high plasmid production (6-11 mg/L/$OD_{600}$) after biomass production. High specific yields are very desirable since increased plasmid yield per gram of bacteria leads directly to higher final product purities.

These results demonstrate the general utility of the fed-batch and batch fermentation processes of the invention to improve plasmid DNA productivity and quality.

Thus, the reader will see that the production processes of the invention provide methods for improved plasmid production.

While the above description contains many specificities, these should not be construed as limitations on the invention, but rather as an exemplification of one preferred embodiment thereof. Many other variations are possible. For example, the inducible fed-batch process can be integrated with the batch process, such that fermentation is done in the NTC3018 batch media until nutrient depletion, whereupon the fed-batch media from NTC3019 and induction are simultaneously initiated. In this embodiment, with some plasmids, the growth phase can be performed at up to 37° C. since plasmid copy number will be reduced with the higher growth rate. The optimal temperature to allow cell division during the growth phase, and retain plasmid inducibility during the fed-batch phase, can be determined by one skilled in the art. Accordingly, the scope of the invention should be determined not by the embodiments illustrated, but by the appended claims and their legal equivalents.

We claim:

1. A method for fed-batch fermentation production of covalently closed super-coiled plasmid DNA comprising the steps of: A) growing bacterial cells containing a plasmid, cosmid, or bacterial artificial chromosome replicon at a reduced temperature during a fed-batch phase; and B) restricting growth rate of the bacterial cells during the fed-batch phase by nutrient limitation; and C) inducing plasmid production by increasing temperature; and D) continuing growth at elevated temperature to accumulate plasmid product; whereby said method increases plasmid yield above yields that are achieved when growing the bacterial cells without the reduced temperature during the fed-batch phase, the reduced temperature during the fed-batch phase being approximately 30° C.

2. The method of claim 1 wherein the reduced temperature during the fed-batch phase is that determined to maintain the plasmid yield below approximately 2 mg/L/$OD_{600}$.

3. The method of claim 1 wherein the plasmid contains a ColE 1 replication origin.

4. The method of claim 1 wherein the plasmid contains a pMB 1 replication origin containing a pUC G to A mutation.

5. The method of claim 1 wherein the plasmid is a VR1012 plasmid.

6. The method of claim 1 wherein the growing bacterial cells are grown in a fermentation media which is semi-defined glycerol media.

7. A method for fermentation production of covalently closed super-coiled plasmid DNA comprising the steps of: A) growing bacterial cells containing a pBR322 plasmid, cosmid, or bacterial artificial chromosome replicon in fed-batch fermentation media, the fermentation media being a semi-defined glycerol media; and B) restricting growth rate during fed-batch phase by nutrient limitation; and C) continuing growth to accumulate plasmid product.

* * * * *